(12) United States Patent
Dam et al.

(10) Patent No.: US 8,085,463 B2
(45) Date of Patent: Dec. 27, 2011

(54) PROTECTIVE COATING FOR METALHYDRIDE BASED DEVICES

(75) Inventors: Bernard Dam, The Hague (NL); Marinus Johannes Slaman, Waddinxveen (NL); Mathieu Raymond Henri Pasturel, Rennes (NL); Herman Schreuders, Alphen aan den Rijn (NL)

(73) Assignee: Stichting Energieonderzoek Centrum Nederland, Le Petten (NL)

( * ) Notice: Subject to any disclaimer, the term of this patent is extended or adjusted under 35 U.S.C. 154(b) by 206 days.

(21) Appl. No.: 12/298,700

(22) PCT Filed: Apr. 25, 2007

(86) PCT No.: PCT/NL2007/050182
§ 371 (c)(1),
(2), (4) Date: Mar. 16, 2009

(87) PCT Pub. No.: WO2007/126313
PCT Pub. Date: Nov. 8, 2007

(65) Prior Publication Data
US 2010/0014151 A1      Jan. 21, 2010

(30) Foreign Application Priority Data
Apr. 27, 2006  (NL) ..................... 1031708

(51) Int. Cl.
*G02F 1/00*   (2006.01)
(52) U.S. Cl. .................. 359/321; 359/228; 359/614
(58) Field of Classification Search .......... 359/227, 359/228, 237, 321, 601, 602, 614; 204/192.15; 356/437
See application file for complete search history.

(56) References Cited

U.S. PATENT DOCUMENTS

| | | | |
|---|---|---|---|
| 5,034,289 A | 7/1991 | Yuasa et al. | |
| 5,230,898 A * | 7/1993 | Horstmann et al. | 424/449 |
| 5,783,152 A | 7/1998 | Nave | |
| 6,006,582 A * | 12/1999 | Bhandari et al. | 73/23.2 |
| 6,310,725 B1 * | 10/2001 | Duine et al. | 359/585 |
| 6,762,871 B2 * | 7/2004 | Yoshimura | 359/265 |
| 2002/0044717 A1 | 4/2002 | Richardson | |
| 2003/0169476 A1 | 9/2003 | Yoshimura | |

(Continued)

FOREIGN PATENT DOCUMENTS

EP        0 386 305        9/1990

(Continued)

OTHER PUBLICATIONS

Janner A-M. et al., "Cycling durability of switchable mirrors", Electrochimica Acta, Elsevier Science Publisher Barking, GB, vol. 46, No. 13-14, Apr. 2, 2001, pp. 2173-2178.

(Continued)

*Primary Examiner* — Loha Ben
(74) *Attorney, Agent, or Firm* — Young & Thompson

(57) ABSTRACT

A thin film device includes an active layer (4), wherein the active layer has optical properties that change by adding and removing hydrogen, and includes a Mg-transition metal layer, or rare earth based layer, the active layer being provided on one side with a protective layer (3) that is hydrogen, oxygen and water vapor permeable and liquid water impermeable, and has hydrophobic surface properties. The thin film can further include a Pd catalyst layer (5) disposed between the active layer (4) and the protective layer (3). The thin film device can be used in a switchable mirror wherein the optical properties of the mirror can be changed by adding/removing hydrogen to/from the active layer.

17 Claims, 1 Drawing Sheet

U.S. PATENT DOCUMENTS

2003/0227667 A1 12/2003 Ouwerkerk et al.
2008/0291452 A1* 11/2008 Dam et al. .................... 356/437

FOREIGN PATENT DOCUMENTS

| EP | 1 345 071 | 9/2003 |
|----|-----------|--------|
| WO | 02/14921 | 2/2002 |

OTHER PUBLICATIONS

Slack et al., "Metal hydride switchable mirrors: Factors influencing dynamic range and stability", Solar Energy Materials and Solar Cells, Elsevier Science Publishers, Amsterdam, NL, vol. 90, No. 4, Mar. 6, 2006, pp. 485-490.

Hughes R. C. et al., "Thin film porous membranes for catalytic sensors", 1997 International Conference on Solid-State Sensors and Actuators. Digest of Technical Papers, Transducers 97, Chicago, IL, Jun. 16-19, 1997, Sessions 3A1.01-4D3.14P, International Conference on Solid-State Sensors and Actu, vol. 2, pp. 581-584.

International Search Report dated Aug. 20, 2007, from corresponding PCT application.

* cited by examiner

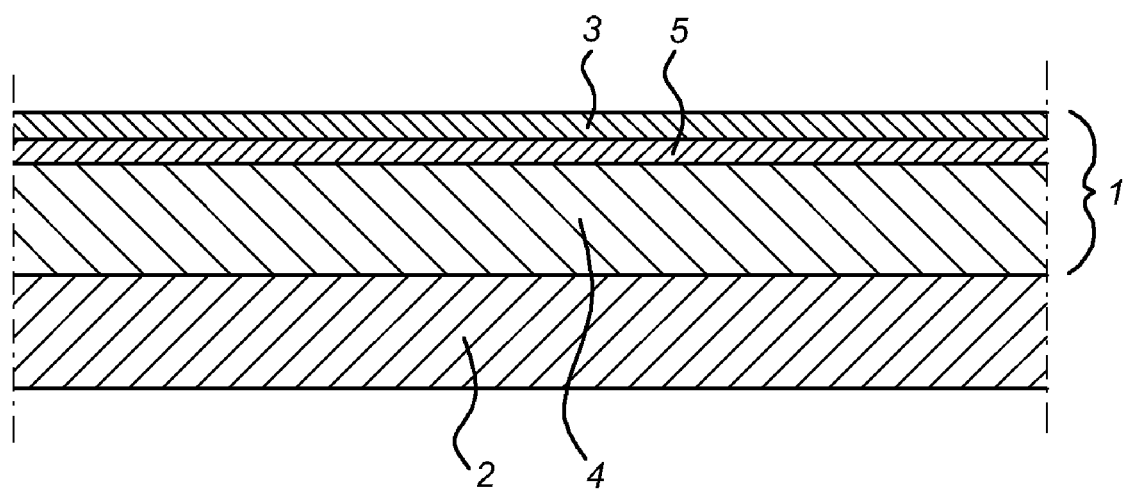

PROTECTIVE COATING FOR METALHYDRIDE BASED DEVICES

The present invention relates to a thin film device.

Such a thin film device is known from EP 1345071. In that patent specification, a switchable mirror is disclosed having an active layer comprising magnesium-nickel (Mg—Ni). The Mg—Ni metal layer is provided on a substrate, and on the other side of the metal layer, a catalyst or protective layer such as palladium (Pd) can be provided. Optionally, the two layers are separated by a third layer, through which hydrogen can diffuse. The optical properties of the active layer depend on the hydrogen content and can be changed, e.g., from transparent to absorbing black to reflective by adding/removing hydrogen. These changes in properties are promising for many applications wherein a repeated change from transparent to reflective is desirable, such as smart windows or hydrogen sensors.

However it has been observed that reproducibility is a problem and at cycling either the quality of the desirable condition deteriorates or the process of switching slows down.

The subject invention aims to remove this drawback and to provide a thin film device in which an increased number of cycles can be effected without deterioration of the desired properties.

These features are realized with a thin film device according to the present invention.

According to the present invention, a protective layer is provided, on the one hand allowing for free conveyance of hydrogen in and from the active layer, but on the other hand, blocking transport of liquids such as water. Furthermore, the surfaces of the protective layer prevent the formation and attachment of liquid water droplets.

It is assumed that the improved properties obtained by the invention are based on the fact that for removal of hydrogen generally oxygen or an oxygen containing gas is used. Oxygen combines with hydrogen and the resulting water can hamper functioning of the active layer if it is in liquid condition. This water can result in corrosion because of the formation of e.g., hydroxides on the surface of the active layer. Water vapor should be able to migrate through the liquid water impermeable layer. Preferably the opening size in the additional layer according to the invention is such that water vapor and the standard conditions can migrate with a speed of $2 \cdot 10^{-6}$ 1 $H_2O$ vapor/$cm^2 \cdot$sec.

It is emphasized that the claimed invention is independent from the correctness of this theory.

Surprisingly, it has been found that through the use of such protective layer, a large number of cycles under the most severe circumstances of the thin film can be effected without deteriorating properties thereof. Also, handling of the thin film is improved because the protective layer provides protection of the active layer being there below. Also, the effectiveness of the catalyst which is covered with the protective layer or coating according to the invention is not affected.

Effectiveness of the invention can be further improved by including scavengers in the protective layer. As example, the presence of sulphur spheres is mentioned in the protective layer for scavenging sulphur in hydrogen sulfide ($H_2S$) which poisons the catalyst below the protective layer.

Furthermore is has been observed that a further protective layer having a thickness between 10-100 nm does not have any negative effect on the rate of entry of hydrogen in the transition metal layer or its removal therefrom. Depending on the material of the further layer the thin film device can be used at both low and high temperatures.

According to a preferred embodiment of the invention, the device is used as an optical switchable mirror. The transmission, reflection or absorbtion of the device is changed by adding or removal of hydrogen. In case of a change in transmission, the protective layer transmits light in order to obtain the optical switching effect. In particular, the application could be in gasochromic smart windows based on gadolinium-magnesium (GdMg)-hydride as the active layer.

Alternatively, combinations are possible with solar collectors to control the light absorption and maintain the operation temperature within a required range. Such embodiments preferably comprise a Mg-transition metal alloy such as magnesium-titanium (Mg—Ti) being arranged on a substrate, on which a catalyst layer comprising Pd is arranged. This catalyst can comprise pure Pd or mixtures thereof. For example, silver (Ag) can be added in a quantity of for example 20-30%.

Depending on the hydrogen concentration, the active layer switches from reflective to absorbing. The protective layer as discussed above is arranged on the Pd-material. The protective or further layer preferably comprises a plastic material and has a thickness of 10 nm to 1 µm, and more particular particularly, about 50 nm.

It has been observed that by using the protective coating the stability of the films in basics solutions against delamination is extended to neutral and acid solutions.

The hydrophobic protective layer according to the invention can be arranged on the thin film with any method known in the art. Preferably, sputtering is used. More particularly, sputtering is used if TEFLON® is used as protective layer. Other methods of depositing are spin coating and so on. As indicated above, TEFLON® (polytetrafluoroethylene) is a preferred material for use as protective layer.

Except from protection against the ingress of liquid water in the active layer through the use of a protective layer, ingress of impurity molecules, such as for example methane (CH4) or large molecules such as those originating from plastics, are prevented.

In the FIGURE an example of the invention is shown.

The thin film device according to the invention is generally indicated by 1 and is provided on a substrate 2. This device comprises a magnesium transition layer 4 on which a catalyst Pd layer 5 is provided.

The hydrophobic layer according to the invention is indicated by 3 and is provided on top of both layers.

Although the invention has been disclosed referring to specific applications and specific lay out of the thin film device, persons skilled in the art will immediately realize that further developments are possible being within the scope of protection of subject application of which the scope of protection is defined by the following claims.

The invention claimed is:

1. A thin film device, comprising:
   a substrate;
   an active layer provided on the substrate, comprising a magnesium (Mg)-transition metal layer, or rare earth based layer, the active layer having optical properties that change depending on hydrogen content; and
   a protective layer provided on the active layer, the protective layer being hydrogen, oxygen and water vapor permeable, and liquid water impermeable, and having hydrophobic surface properties, said protective layer comprising a scavenger.

2. The device according to claim 1, wherein said Mg-transition metal layer comprises Mg-titanium (Mg—Ti).

3. A hydrogen sensor, comprising the device according to claim 1.

4. The device according to claim 1, wherein said protective layer is substantially light transmitting.

5. The device according to claim 1, wherein said Mg-transition metal layer comprises nickel (Ni).

6. The device according to claim 1, wherein said active layer further comprises a palladium (Pd) catalyst layer.

7. The device according to claim 6, further comprising a third layer, through which hydrogen can diffuse, provided between the Pd catalyst layer and the Mg-transition metal layer.

8. The device according to claim 6 wherein said Pd catalyst layer comprises silver (Ag).

9. The device according to claim 8, wherein said Pd catalyst layer comprises 20-30% Ag.

10. The device according to claim 1, wherein said protective layer has a thickness of 10 nm-1 µm.

11. The device according to claim 10, wherein said protective layer has a thickness of 10-100 nm.

12. The device according to claim 10, wherein said protective layer has a thickness of about 50 nm.

13. The device according to claim 1, wherein said protective layer comprises a polymer material.

14. The device according to claim 1, wherein said protective layer comprises polytetrafluoroethylene.

15. The device according to claim 1, wherein said scavenger is a sulphur scavenger.

16. A switchable mirror, comprising the thin film device according to claim 1, wherein the optical properties of the mirror can be changed by adding/removing hydrogen to/from the active layer.

17. A method for producing a thin film device having an active layer, the active layer having optical properties that change depending on hydrogen content, the method comprising:

providing a substrate, depositing said active layer on said substrate, the active layer comprising (i) a magnesium (Mg)-transition metal layer or a rare earth based layer, and (ii) an outermost catalytic palladium (Pd) layer, and arranging a protective layer on the outermost catalytic Pd layer, wherein said protective layer is arranged by sputtering.

* * * * *